United States Patent [19]

Ivko et al.

[11] 4,274,165
[45] Jun. 23, 1981

[54] SELF-ALIGNING CABLE GUIDE ASSEMBLY

[76] Inventors: Joseph J. Ivko; Renette Ivko, both of 1644 Magellan Dr., Sarasota, Fla. 33589

[21] Appl. No.: 120,155

[22] Filed: Feb. 11, 1980

[51] Int. Cl.³ .............................................. A61F 1/06
[52] U.S. Cl. ......................................... 3/12; 254/415; 254/389
[58] Field of Search .......................... 3/12, 12.1–12.8; 254/415, 389; 226/196; 43/24; 242/157 R

[56] References Cited

U.S. PATENT DOCUMENTS

| | | | |
|---|---|---|---|
| 1,950,074 | 3/1934 | Wheeler | 254/415 |
| 2,834,024 | 5/1958 | Areni | 3/12 |
| 3,128,992 | 4/1964 | Luketa | 254/415 |
| 3,215,405 | 11/1965 | Walsh | 254/389 |
| 3,388,891 | 6/1968 | DeMeo | 254/415 |

FOREIGN PATENT DOCUMENTS 240617 10/1925 United Kingdom ..................... 254/415

*Primary Examiner*—Clifford D. Crowder
*Attorney, Agent, or Firm*—Richard R. Mybeck

[57] ABSTRACT

An improved cable guide assembly applicable to machinery, scientific instruments and prosthetic devices. When subjected to varying rotational and directional cable stress the assembly has the ability to automatically align itself so that cable stress is minimized. The assembly is particularly applicable to prosthetic devices and, in addition to extending cable life in such devices from six weeks or less to more than one year, the occasional changing of the cables is remarkably facilitated.

12 Claims, 14 Drawing Figures

U.S. Patent  Jun. 23, 1981  Sheet 1 of 2  4,274,165
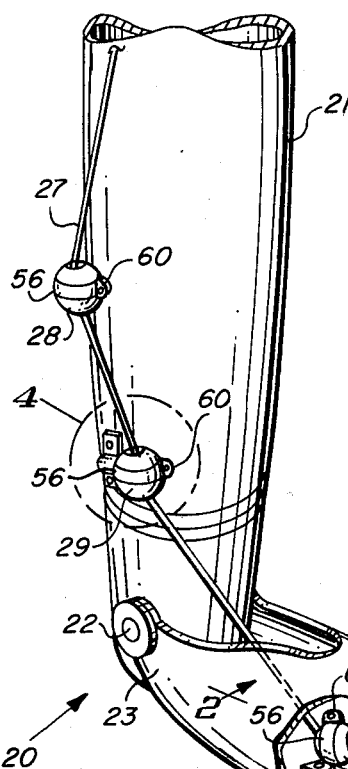
FIG. 1
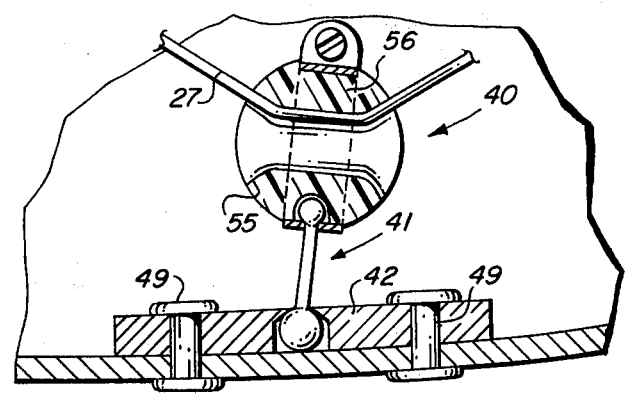
FIG. 2
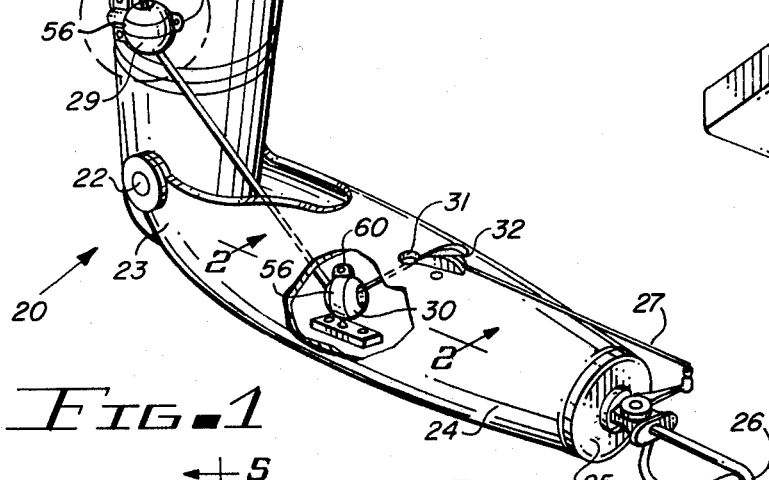
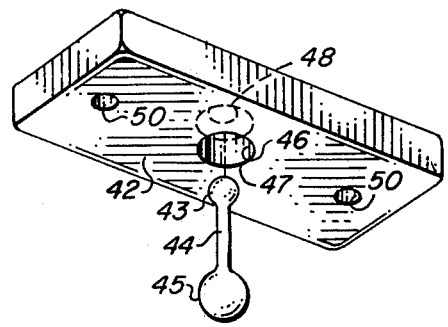
FIG. 3
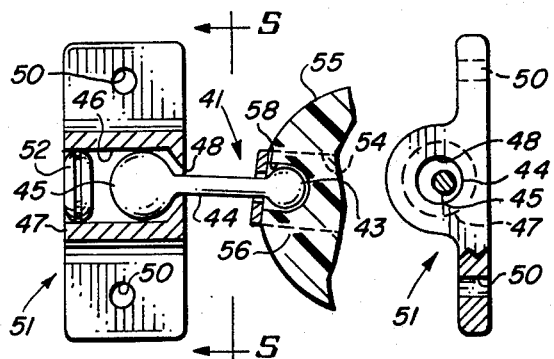
FIG. 4  FIG. 5
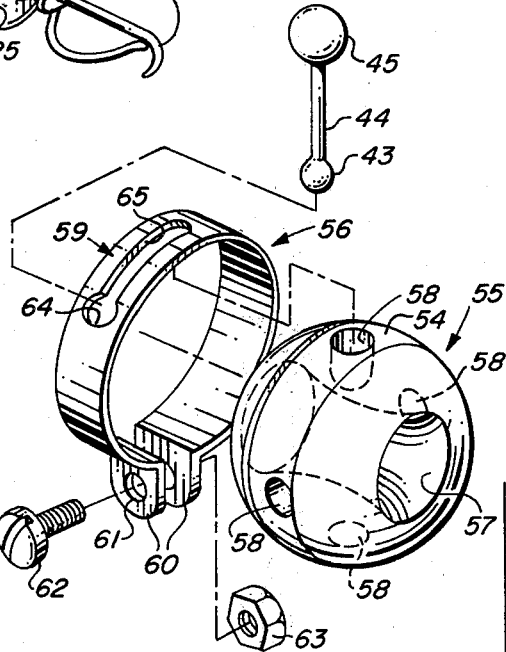
FIG. 6
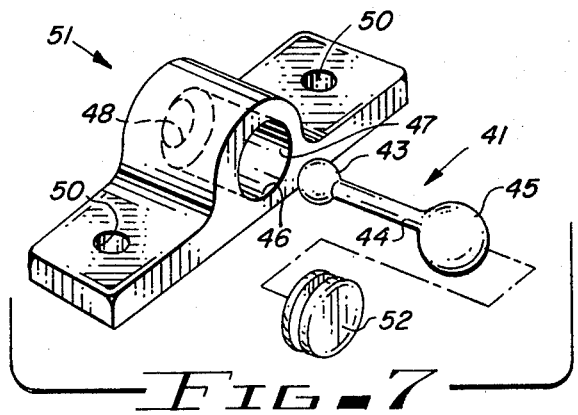
FIG. 7
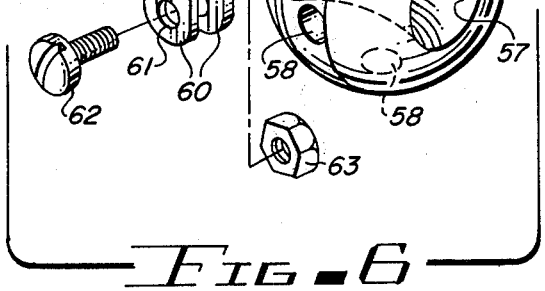

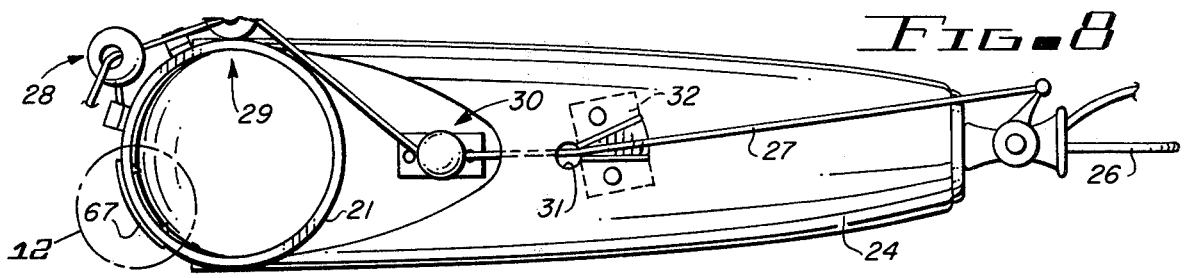
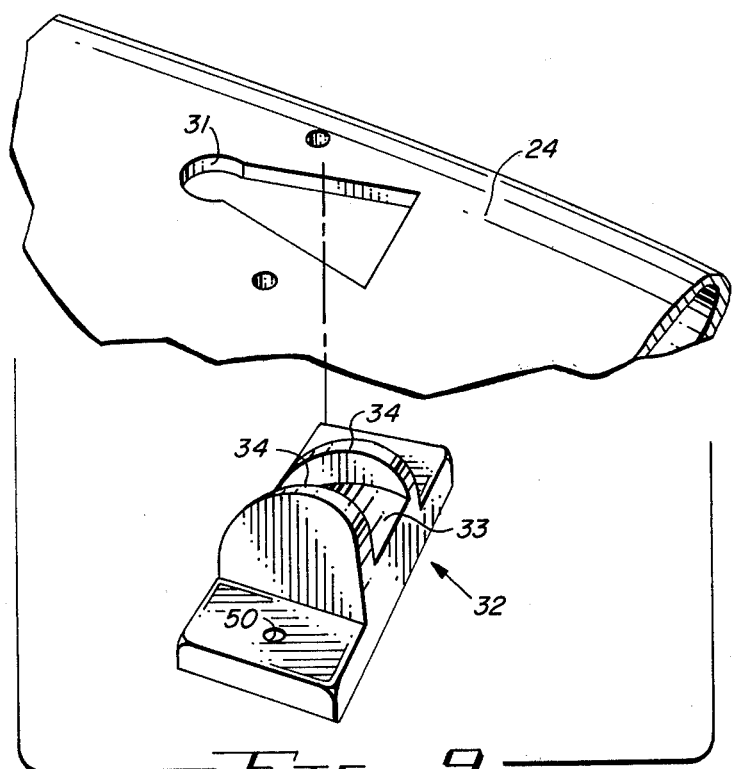
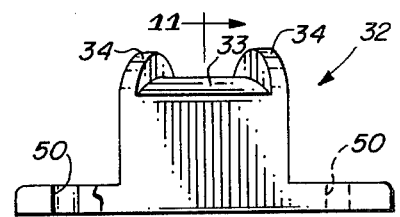
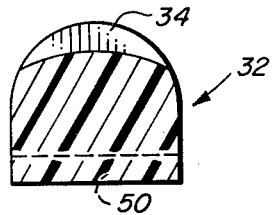
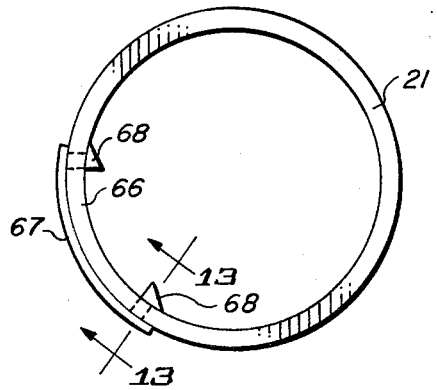
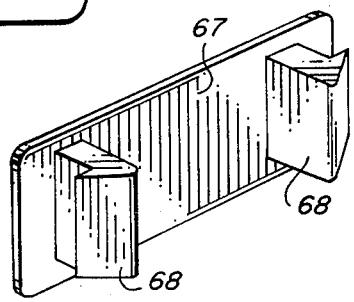

SELF-ALIGNING CABLE GUIDE ASSEMBLY

The present invention relates to cable guides and more particularly to a new and improved cable guide assembly having the ability to align itself along the operative axis of the cable to thereby minimize the stress placed on the cable, whereupon the life of the cable is substantially increased. Still more particularly, the present invention relates to a cable guide assembly which is especially well suited for use on a prosthetic device.

Cable guides which are presently in use on machinery, scientific instruments, ordinary prosthetic devices and other apparatus generally consist of tubular housings through which the cable moves. When the cable moves approximately back and forth in a rectilinear path, such cable guides are normally satisfactory. However, when a cable is subjected to angular movement relative to the tubular axis of the housing, an abnormal stress is placed upon the cable and its useful life is substantially and dramatically reduced.

Such stress/abrasion-induced cable failure is a common problem with cables used to activate prosthetic devices worn by uni- and bilateral upper arm amputees for these devices subject the cable to a variety of stresses. One prior art practice of attempting to alleviate wear and stress on the cable comprises lining the interior surface of a cable sheath or housing with a Teflon liner. However, when the Teflon liner wears out, the cable again wears directly upon the steel housing, thus causing the cable to abrade quickly so that frequent cable replacement is required. Because cables are quite expensive and are difficult to reinstall, the user of such a prosthetic device is constantly subjected to the uncertainty and frustration of worrying about an inopportune break down of the cable system which would prevent him from performing normal functions with his prosthetic device.

Accordingly, a need still exists to provide means for guiding a cable in such a way that the deleterious effect of wear resulting from the metal cable riding back and forth across a metal housing is eliminated. It is to the fulfillment of that need that the present invention is directed.

It has been discovered that when conventional cable sheaths are replaced by the improved cable guide assemblies of the present invention, that is, by cable guide assemblies which have the ability to automatically align themselves with the varying directional stresses placed upon the cable guided thereby during use, the life expectancy of such a cable is dramatically increased from a presently expected life span of 3-6 weeks (when used in a prosthetic device) to a life span of one year or more. Furthermore, the use of cable sheaths is avoided and the installation of new cables, when changes are required, is greatly facilitated.

Accordingly, a primary object of the present invention is to provide an improved, relatively friction-free, self-aligning cable guide assembly which is adaptable for use in a variety of machines, scientific instruments and prosthetic devices.

A further object of the present invention is to provide an improved cable guide assembly which is particularly applicable to prosthetic devices designed for uni- and bilateral upper arm amputees, and which provides improved cable life, reduced maintenance costs and greatly diminished down time.

Yet another object of the present invention is to provide a cable guide assembly which reduces the frustration and worry of an amputee over an inopportune break down of the cable system, thereby allowing the amputee to lead a more normal and less anxious life.

These and still other objects, as shall hereinafter appear, are fulfilled by the present invention in a remarkably unexpected fashion as can be readily discerned from a careful consideration of the following detailed description of exemplary embodiments thereof, especially when read in conjunction with the accompanying drawings in which like parts bear like indicia throughout the several views.

BRIEF DESCRIPTION OF THE DRAWINGS

FIG. 1 is a perspective view of a prosthetic device equipped with three cable guide assemblies, each of which embodies the present invention;

FIG. 2 is a cross-sectional view of a first cable guide assembly taken along line 2—2 of FIG. 1;

FIG. 3 is an exploded view of the connecting piece and the base plate of the cable guide assembly shown in FIG. 2;

FIG. 4 is a detail, partially in section, of a second cable guide assembly as identified by the circle 4 in FIG. 1;

FIG. 5 is a side view, partially in section, of the base plate of a cable guide assembly taken along lines 5—5 of FIG. 4;

FIG. 6 is an exploded view of a guide ball assembly with connecting piece, made in accordance with the present invention;

FIG. 7 is a perspective view, partially in section, of a base plate, connecting piece and plug of the embodiment shown in FIGS. 4 and 5;

FIG. 8 is plan view, partially in section, of the prosthetic device shown in FIG. 1;

FIG. 9 is an exploded perspective view of a wedge guide and a forearm shell of the prosthetic device shown in FIGS. 1 and 8;

FIG. 10 is an end view of a wedge guide taken from the wrist end of the forearm shell shown in FIG. 8;

FIG. 11 is a side view, partially in section, of the wedge guide taken along line 11—11 of FIG. 10;

FIG. 12 is a plan view of the prosthetic upper arm shell shown in FIG. 8, illustrating the covered access opening therein as identified by the circle 12 of FIG. 8;

FIG. 13 is a cross-sectional side view of the access opening, with dust cover installed, taken along lines 13—13 of FIG. 12; and FIG. 14 is a perspective view of the dust cover of FIG. 12.

DETAILED DESCRIPTION OF PREFERRED EMBODIMENTS

A prosthetic device, identified by the general reference 20, having a cable guide system embodying the cable guide assembly of the present invention is illustrated in FIG. 1. The device 20 comprises an upper arm shell 21 which is attached to an amputee by means well known in the art. The upper arm shell 21 is pivotally attached at an elbow 22 to the proximal end 23 of the lower arm shell 24, and attached to the distal end 25 of the lower arm shell 24 is a hook 26. The hook 26 is operably controlled by a cable 27 which passes successively from the shoulder harness (not shown) of the prosthetic device 20 through three cable guide assemblies 28, 29 and 30, through an opening 31, across a wedge guide 32 and to the hook 26, where it is attached. The cable 27 rides in a channel 33 of the wedge guide 32 and is retained therein by the channel edges 34 (FIGS. (9–11). The wedge guide 32 is disposed on the interior surface of the lower arm shell 24 and the channel portion of the wedge guide protrudes upwardly through the opening 31. Of course, it must be understood that when devices such as prosthetic device 20 are utilized by a bilateral amputee, the cable guide system embodying the present invention may be employed in each such device without significant alteration.

The embodiment of the present invention represented by the assembly 30 is illustrated in greater detail in FIG. 2. The guide ball assembly 40, as hereinafter defined, is operatively attached to a connecting piece 41, which in turn is operatively attached to a base plate 42. Connecting piece 41 is formed generally in the shape of a dog bone, having a relatively smaller distal end 43, an elongated body portion 44, and a proximal end 45, said proximal end 45 being relatively larger than the distal end 43. As illustrated in FIGS. 2 and 3, the base plate 42 has a cavity 46 therein, said cavity 46 having a first opening 47 and a second constricted opening 48. For convenience, base plate 42 will be referred to as "top mounting" because the connecting piece 41 extends vertically from the top surface thereof. Other base plates 51, as hereinafter described (FIGS. 4 and 7), will be referred to as "side mounting" since connecting piece 41 extends laterally from the side surface thereof. Base plate 42 is fastened to the arm shell 24 by appropriate fastening means 49, such as screws, bolts, rivets and the like which pass through suitable openings 50 defined through base plate 42 adjacent to each end thereof. It must be understood, however, that base plates 42 and 51 are only representative, and that other means may also be used to operatively associate the proximal end 45 of the connecting piece 41 with a support surface.

Connecting piece 41 is operatively retained in base plate 42 by inserting the distal end 43 into the first opening 47, through the cavity 46 and out the constricted opening 48. Distal end 43 is small enough to pass through opening 48; however, proximal end 45 is of sufficient size that it will fit into cavity 46 but will not pass through opening 48. When base plate 42 is attached to an arm shell by inserting fastening means 49 through holes 50, connecting piece 41 is retained in cavity 46. Thus, the connecting piece 41 can be rotated, wobbled, orbited slightly about its proximal end or otherwise moved in a limited fashion within cavity 46, but it cannot come out of said cavity. Similarly, FIGS. 4 and 7 illustrate a side-mounting base plate 51 in which a connecting piece 41 is retained. However, since the opening 47 to cavity 46 is not closed off when base plate 51 is attached to an arm shell, connecting piece 41 must be retained therein by other means, such as by a plug 52.

From FIG. 6 it may be seen that the guide ball assembly 40 is comprised of two major components: a ball 55 and a retaining band 56. In one embodiment, the guide ball 55 is approximately one inch in diameter, is generally spherical in shape and is constructed of a durable and non-abrasive material such as nylon or like material. A cable guide hole 57, through which the cable 27 passes, is defined through the guide ball 55 coaxially with a diameter thereof so as to pass through the center of guide ball 55. Hole 57 is flared at each end thereof so that cable drag therethrough and cable wear therefrom are reduced. Disposed generally perpendicular to the axis of hole 57 and about the circumference of the guide ball 55 is at least one, but preferably a plurality of, recessed areas 58 which are of sufficient size to engage and receive the distal end 43 of the connecting piece 41 in a manner to be hereinafter described in a greater detail.

Retaining band 56 is preferably constructed of a durable yet corrosion-resistant material such as stainless steel or the like, is generally shaped to conform to the peripheral surface of spherical ball 55, has a keyway 59 defined therethrough, and extends between flanges 60, each of which has a suitable hole 61 defined therethrough. Band 56 is of such shape that when flanges 60 are fastened together by suitable means, such as nut 62 and bolt 63, band 56 is firmly secured to guide ball 55. Keyway 59 longitudinally occupies approximately 60° of arc on band 56 and is comprised of a mouth portion 64 and a retaining slot portion 65. Mouth 64 is disposed about the arc of band 56 approximately 120° from the mating plane of flanges 60, while retaining slot 65 extends longitudinally from mouth 64 to a point approximately opposite the flanges 60; i.e., to a point approximately 180° about the arc of band 56 from the mating plane of flanges 60.

Mouth 64 has a diameter slightly larger than that of distal end 43 of connecting piece 41, whereas retaining slot 65 is slightly narrower than the diameter of distal end 43 but is slightly wider than the crossectional width of body portion 44. To operably attach guide ball assembly 40 to connecting piece 41, band 56 is loosely placed about the ball 55 (as illustrated in FIG. 2) and the mouth 64 of keyway 59 is aligned with one recessed area 58. Distal end 43 of connecting piece 41 is then inserted into recessed area 58 and band 56 is rotated 55° about the axis of cable guide hole 57, until body portion 44 engages the closed end of retaining slot 65. With band 56 thus located, it is secured in that position by fastening flanges 60 together by tightening bolt 63 in nut 62, and connecting piece 41 is moveably retained in recessed area 58.

Preferably, as illustrated in FIG. 6, the exterior surface of ball 55 is provided with a groove 54 which, as previously indicated, is disposed circumferentially about the axis of the cable guide hole 57 so that band 56 can be readily aligned and tightened therein. When thus secured in groove 54, band 56 is prevented from sliding laterally off of ball 55. Furthermore, as previously noted, ball 55 is preferably provided with more than one recessed area 58 so that when the interior surface of cable guide hole 57 begins to show excessive wear from the cable, a new recessed area can be utilized. For example, connecting piece 41 can be easily removed and ball 55 can be rotated about the axis of the cable guide hole 57 until a new recessed area 58 is aligned with mouth 64 of keyway 59, and connecting piece 41 can then be reattached as hereinbefore described. Four such recessed areas are shown in FIG. 6.

As previously explained, at least two different types of base plates will be required, depending on the environment in which a cable guide assembly is used. A side-mounting base plate, such as plate 51 (FIGS. 4 and 7) is intended for use where the cable 27, as it approaches and leaves the guide ball assembly 40, is approximately parallel to the support surface to which base plate 51 is affixed. However, should cable 27 pass through guide ball assembly 40 from above the support surface, a top-mounting base plate such as base plate 42 (FIGS. 2 and 3) would be required. Access to the interior regions of a prosthetic device may be required in order to affix a base plate in an appropriate manner. FIGS. 12 and 13 illustrate a portion of the upper arm shell 21 in which a representative access 66, with a dust cover 67, has been disposed. Cover 67 is frictionally retained in the opening of access 66 by flexible hooks 68 (FIG. 14) which coact with the adjacent portion of arm shell 21.

The advantages of using a cable guide assembly as disclosed herein are immediately apparent. All movements of a prosthetic device are cable actuated, and humeral rotation and vertical movement of an arm shell place varying stresses on a cable. These stresses are variable not only as to amount but also as to direction. However, when a device is equipped with a series of cable guide assemblies as disclosed herein, the deleterious effects on a cable are minimized. The device 20 illustrated in FIG. 1 provides a good example. When tension is placed on cable 27 in order to activate hook 26, each guide ball assembly 40 automatically rotates about connecting piece 41 in such a fashion as to make the contact pressure of cable 27 upon the interior surface of cable guide hole 57 approximately equal at all points where cable 27 contacts said interior surface of ball 55. As guide ball assembly 40 moves, connecting piece 41 is also moveable and aligns itself with the pull of the cable. FIG. 2 is illustrative for it shows that, in response to tension placed on cable 27, the axis of cable guide hole 57 tilted slightly in relation to the upper surface of base plate 42 and, in response to that movement, connecting piece 41 assumed an angular position in relation to base plate 42. Similar movement occurs with all of the cable guide assemblies so that, rather than having points of abrasion as found with conventional prior art cable sheaths, generally reduced and uniform stress is placed on the cable where it contacts guide ball 55. As a result, the life of cable 27 is lengthened in a remarkable manner. For example, although the cable life in a conventional cable system is typically 3-6 weeks, the cable life of a cable used with the cable guide assembly as disclosed herein can exceed one year.

In addition, a particularly attractive feature of the cable guide assembly is that, when a cable eventually does break down, its replacement is remarkably simple. The cable is merely unhooked from hook 26, pulled across wedge guide 32, through opening 31, through the series of cable guide assemblies and is then disconnected from the shoulder harness. The new cable is thereafter attached to the harness, rapidly threaded through each guide ball assembly, through opening 31, across wedge guide 32, and then attached to hook 26. The entire replacement time is, under normal conditions, less than two minutes. When compared to the presently available systems in which the cable must be slowly and arduously fed through a series of cable sheaths, the invention described herein is clearly seen to be a significant improvement.

It must be understood that the present invention is not limited to the embodiments described and illustrated herein, and that such modifications, alterations and applications as may readily occur to the skilled artisan confronted with this disclosure are intended within the spirit of the invention which is limited only by the scope of the claims which follow.

What we claim and desire to protect by Letters Patent is:

1. A self-aligning cable guide assembly operatively associated with a support surface and adapted to receive and guide a cable therethrough in a substantially stress-free relationship therewith, said assembly comprising:
   mounting means attachable to a support surface;
   a ball member having a cable guide hole defined therethrough;
   a connecting member operatively associated with said mounting means and extendable outwardly therefrom for operative engagement with said ball member; and
   a band member circumferentially disposed about said ball member for operative engagement with said ball member to secure said connecting member to said ball member.

2. An assembly according to claim 1 in which said connecting member comprises a distal end for operative association with said ball and band members, a proximal end for operative association with said mounting means, and a body portion interconnecting said distal end and said proximal end.

3. An assembly according to claim 2 in which said distal end and said proximal end of said connecting member comprise generally spherical portions, said distal sphere having a relatively smaller diameter than said proximal sphere.

4. An assembly according to claim 2 in which said ball member has a plurality of interchangeable recessed areas disposed thereabout to engage and receive said distal end of said connecting member therein.

5. An assembly according to claim 4 in which said cable guide hole is flared at each end thereof.

6. An assembly according to claim 4 in which said ball member is constructed of a durable and non-abrasive material.

7. An assembly according to claim 2 in which said mounting means comprises a base plate attachable to a support surface and having a cavity disposed therein, said cavity having a first opening and a second opening thereto to receive said connecting member therewithin, said second opening being constricted relative to said first opening to secure said connecting member relative thereto.

8. An assembly according to claim 7 in which said connecting member extends upwardly from said base plate.

9. An assembly according to claim 7 in which said connecting member extends laterally from said base plate.

10. An assembly according to claim 1 in which said band member comprises an elongated strip disposed in general conformity to the peripheral surface of said ball member, said band member having a keyway defined circumferentially thereof and extending therethrough to receive and secure said connecting member relative to said ball member, said keyway being disposed intermediate the edges of said strip and having an enlarged mouth portion at one end thereof.

11. An assembly according to claim 10 in which said band member is constructed of a durable and corrosion-resistant material.

12. In a cable prosthetic device usable by uni- and bilateral upper arm amputees, said device having:
   an upper arm shell having a shoulder end and an elbow end;
   a lower arm shell having an elbow end and a wrist end and moveably hinged to said upper arm shell at said elbow end;
   a cable-activated hand attached to said lower arm shell; and a cable, one end thereof being attached to said hand and the other end thereof being attachable to, and activatable by, said amputee, the improvement comprising the disposal at strategic locations on said upper arm shell and said lower arm shell of a plurality of self-aligning cable guide assemblies comprising mounting means attachable to one of said shells;
- a ball member having a cable guide hole defined therethrough;
- a connecting member operatively associated with said mounting means and extendable outwardly therefrom for operative engagement with said ball member; and
- a band member circumferentially disposed about said ball member for operative engagement with said ball member to secure said connecting member to said ball member, and a wedge guide operatively disposed between one of said assemblies and said hand, whereupon said cable is conducted in a relatively stress-free condition from said amputee to said hand.

* * * * *